(12) United States Patent
Delmenico et al.

(10) Patent No.: US 9,575,078 B2
(45) Date of Patent: Feb. 21, 2017

(54) METHOD FOR HEMOSTASIS TESTING

(71) Applicant: Coramed Technologies, LLC, Niles, IL (US)

(72) Inventors: Peter Delmenico, Chicago, IL (US); Carlos G. Lopez-Espina, Evanston, IL (US); Gabriel Raviv, Glenview, IL (US)

(73) Assignee: Coramed Technologies, LLC, Glenview, IL (US)

( * ) Notice: Subject to any disclaimer, the term of this patent is extended or adjusted under 35 U.S.C. 154(b) by 67 days.

(21) Appl. No.: 14/212,891

(22) Filed: Mar. 14, 2014

(65) Prior Publication Data
US 2015/0260735 A1    Sep. 17, 2015

Related U.S. Application Data

(60) Provisional application No. 61/792,349, filed on Mar. 15, 2013.

(51) Int. Cl.
*G01N 33/86* (2006.01)
*G01N 33/48* (2006.01)
(Continued)

(52) U.S. Cl.
CPC ......... *G01N 33/86* (2013.01); *G01N 33/4905* (2013.01); *B01L 3/50273* (2013.01); *B01L 3/502753* (2013.01); *G01N 29/036* (2013.01); *G01N 2291/02818* (2013.01); *G01N 2291/02827* (2013.01); *G01N 2291/0427* (2013.01); *G01N 2800/224* (2013.01)

(58) Field of Classification Search
CPC .... G01N 33/48; G01N 33/49; G01N 33/4905; G01N 33/86; G01N 2291/02818; G01N 2291/02827; G01N 2291/0427; G01N 2800/224; G01N 29/036; B01L 3/502753; Y10T 436/25; Y10T 436/2575
USPC ...... 436/63, 69, 174, 180; 422/73, 502, 503, 422/504, 505, 537, 554; 435/13; 600/369; 73/64.41, 64.42
See application file for complete search history.

(56) References Cited

U.S. PATENT DOCUMENTS 5,494,639 A * 2/1996 Grzegorzewski ...... G01N 9/002
                                                    422/502
6,200,532 B1 * 3/2001 Wu ...................... G01N 29/036
                                                    422/73
(Continued)

Primary Examiner — Maureen Wallenhorst

(57) ABSTRACT

A sample testing cartridge is usable to perform a variety of tests on a visco-elastic sample, such hemostasis testing on a whole blood or blood component sample. The cartridge includes a sample processing portion that is in fluid communication with a sample retention structure. A suspension, such as a beam, arm, cantilever or similar structure supports or suspends the sample retention portion relative to the sample processing portion in a unitary structure. In this manner, the sample retention portion may be placed into dynamic excitation responsive to excitation of the cartridge and correspondingly dynamic, resonant excitation of the sample contained within the sample retention portion, while the sample processing portion remains fixed. Observation of the excited sample yields data indicative of hemostasis. The data may correspond to hemostasis parameters such as time to initial clot formation, rate of clot formation, maximum clot strength and degree of clot lysis.

21 Claims, 4 Drawing Sheets

(51) Int. Cl.
*G01N 33/49* (2006.01)
*B01L 3/00* (2006.01)
*G01N 29/036* (2006.01)

(56) References Cited

U.S. PATENT DOCUMENTS

| | | | | |
|---|---|---|---|---|
| 6,797,519 | B2 * | 9/2004 | Cohen | G06Q 50/22 422/73 |
| 7,261,861 | B2 * | 8/2007 | Kautzky | G01N 33/4905 422/73 |
| 7,879,615 | B2 * | 2/2011 | Kautzky | G01N 11/167 422/73 |
| 8,236,568 | B2 * | 8/2012 | Kautzky | G01N 33/4905 422/73 |
| 9,068,966 | B2 * | 6/2015 | Delmenico | G01N 33/4905 |
| 2007/0059212 | A1 * | 3/2007 | Masters | G01N 29/036 422/88 |
| 2010/0015649 | A1 * | 1/2010 | Day | G01N 9/002 435/13 |
| 2011/0203367 | A1 * | 8/2011 | Huang | G01N 33/4905 73/32 R |
| 2012/0252043 | A1 * | 10/2012 | Gehring | G01N 29/036 435/13 |

\* cited by examiner

METHOD FOR HEMOSTASIS TESTING

CROSS-REFERENCE TO RELATED APPLICATION

This patent claims priority to U.S. Provisional Patent Application Ser. No. 61/792,349, filed Mar. 15, 2013, entitled Apparatus, Cartridge and Method for Hemostasis Testing, the disclosure of which is hereby expressly incorporated herein by reference.

STATEMENT AS TO RIGHTS TO INVENTIONS MADE UNDER FEDERALLY SPONSORED RESEARCH OR DEVELOPMENT

This invention was made with government support under grants R43HL088850 and R44HL088850, awarded by the National Heart, Lung, and Blood Institute of the National Institutes of Health. The U.S. Government has certain rights to this invention.

TECHNICAL FIELD

This patent relates to blood hemostasis testing, and in particular, this patent relates to sample testing cartridges for preparing and testing blood samples.

BACKGROUND

Blood is in liquid form when traveling undisturbed in bodily passageways. However, an injury may cause rapid clotting of the blood at the site of the injury to initially stop the bleeding, and thereafter, to help in the healing process. An accurate measurement of the ability of a patient's blood to coagulate in a timely and effective fashion and subsequently to lyse is crucial to certain surgical and medical procedures. Also, accurate detection of abnormal hemostasis is of particular importance with respect to appropriate treatment to be given to patients suffering from clotting disorders.

Blood hemostasis is a result of highly complex biochemical processes that transform the blood from a liquid state to a gel state. Characteristics of blood, such as strength of the clot and other mechanical properties of the blood are useful in determining its hemostasis characteristics. For example, if the strength of the clot can resist the shear forces of the circulating blood, that clot can adhere to a damaged vascular site (e.g. open vascular system following surgery) and stop bleeding. That same formed clot in an undamaged (i.e. closed) vascular system will impede the flow of blood and, depending on its location, can cause heart attack, ischemic stroke, pulmonary embolism (PE), or deep vein thrombosis (DVT).

In accordance with commonly owned U.S. Pat. No. 8,236,568 entitled Method of Analyzing Hemostasis; U.S. Pat. No. 7,879,615 entitled Hemostasis Analyzer and Method and U.S. Pat. No. 7,261,861 entitled Hemostasis Analyzer and Method, the disclosures of which are hereby expressly incorporated by reference, a description is provided of apparatus and methods for hemostasis analysis by observation of sample resonant response to dynamic excitation. A blood hemostasis analyzer in accordance with the teachings of these patents operates under the principle that because hemostasis of a blood sample changes the blood sample from a liquid state to a gel state, and the visco-elastic properties of the clot formed by coagulation controls the natural frequency of the sample, measuring changes in the natural frequency of the blood sample during coagulation provides the hemostasis characteristics of the blood sample. In keeping with this principle, the blood hemostasis analyzer measures the changes in the natural frequency of a blood sample during coagulation and lysis to provide hemostasis characteristics of the blood sample. To measure hemostasis in this manner, the analyzer generally includes a container for holding the blood sample, a shaker or exciter for displacing the container to excite the blood sample to resonant vibration, and a sensor for measuring the resulting amplitude of motion of the blood sample.

The above-patented method of hemostasis analysis provides for vibration of a sample to resonance. As blood transitions from a liquid state to a gel state, such as a substantially dilute cross-linked system, exhibiting no flow at steady-state, the natural frequency of the blood sample increases. Hence, measuring the changes in the natural frequency of the sample under excitation and during clotting and lysis provides a hemostasis indication.

SUMMARY

Figure 1:
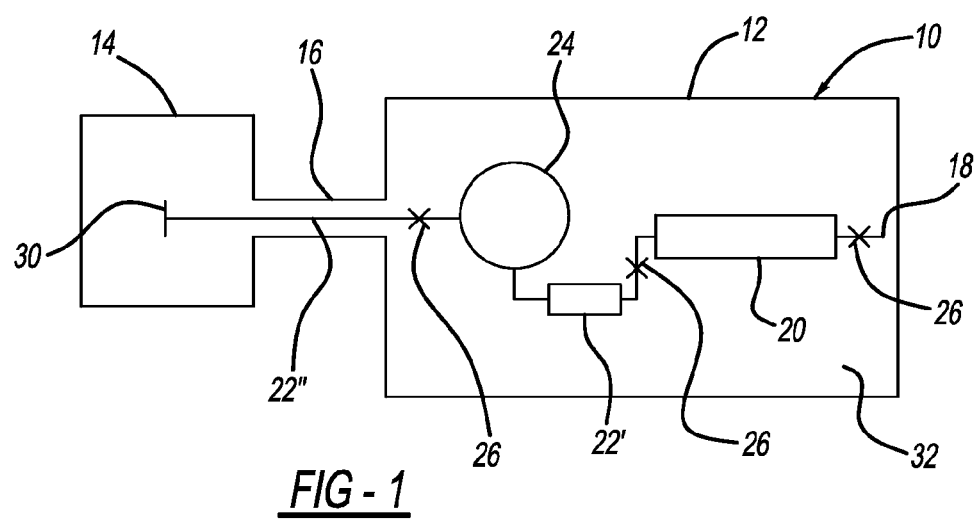
FIG. 1 graphically depicts a cartridge for sample testing in accordance with a herein described embodiment of the invention.

A cartridge for sample testing may include a sample preparation portion including a fluid processing structure and a sample testing portion that includes a sample retention structure. The sample testing portion may be coupled to the sample preparation portion by a fluidic passage providing fluid communication between the fluid processing portion and the sample retention structure. The sample retention structure supports a sample to be tested such that the sample may be excited to resonant vibration responsive to an excitation applied to the cartridge. The sample retention structure also permits observation of the sample excited to resonant vibration.

The cartridge may be coupled to the sample preparation portion such that the sample retention structure may be excited separate and apart from the sample preparation portion. For example, the sample retention structure may be coupled via a suspension to the sample preparation portion.

The cartridge may be an assembly of components. For example, the cartridge may be a laminate structure comprising a number of separate layers joined together.

The fluid processing structure of the cartridge may include operatively arranged a plurality of fluid passages, at least one valve, a bellows and a reservoir. A reagent may be disposed in any one or more of the fluid passage, valve, bellows, reservoir or other portions of the fluid processing structure and multiple combinations thereof.

A valve structure of the cartridge may be a hydrophobic vent surface disposed within a passage or other fluidic structure. Another valve structure may be a flexible membrane disposed within a passage.

The sample retention structure may be an annulus.

A method of testing blood hemostasis may include introducing a blood sample into a fluid processing structure, where the fluid processing structure contains a reagent, for example in a passage. The fluid sample may be processed by passing a portion through the fluid processing structure so as to contact the reagent. The processed portion is then communicated to a sample retention structure of the fluid processing structure. Testing is accomplished by vibratory excitation of the processed portion to obtain data indicative of at least one hemostasis parameter.

The reagent may be disposed within a passage of the fluid processing structure, and processing the sample may be passing the portion through the passage.

The fluid processing structure may include a pump for pumping the portion within the fluid processing structure. The pump may also be used to pump the sample to the sample retention apparatus.

The fluid processing structure may include first and second passages corresponding to first and second tests or assays. In such an arrangement, processing the sample may include communicating a first portion of the blood sample through the first passage and communicating a second portion of the blood sample through the second passage. Likewise, the first and second portions may be communicated to first and second sample retention structures. Simultaneous testing of multiple processed sample portions may be accomplished, for example by exciting the processed portion or portions to resonant vibration. Sample excitation may be accomplished by applying an excitation signal to the cartridge containing the fluid processing structure and the sample retention structure, or by applying an excitation signal only to a portion of the cartridge containing the sample retention structure.

Generated hemostasis data may include parameters at least indicative of one of: time to initial clot formation, rate of clot formation, maximum clot strength and time to clot lysis and degree of clot lysis at a predetermined time after maximum clot strength, e.g., 30 minutes. The data may be communicated to other locations or processors over a network. The data may also or alternatively be depicted graphically.

DETAILED DESCRIPTION

In accordance with the herein described embodiments, a sample-testing cartridge is usable to perform a variety of tests on a viscoelastic sample, such as a whole blood or blood component sample. The cartridge includes a sample-processing portion that is in fluid communication with a sample retention structure. In one embodiment, a suspension, such as a beam, arm, cantilever or similar structure supports or suspends the sample retention portion relative to the sample-processing portion in a unitary structure. The sample-processing portion may be held rigidly so as to permit communication with a source of pneumatic drive as well as user interaction, while the sample retention portion may be placed into dynamic excitation responsive to excitation of the sample retention portion of the cartridge, another portion of the cartridge or the cartridge as a whole. Correspondingly, dynamic, resonant excitation of the sample is achieved within the sample retention portion as a result of such excitation. Observation of the excited sample yields data indicative of the changing elastic properties of the sample. This data may correspond to hemostasis parameters such as time to initial clot formation, rate of clot formation, maximum clot strength, time to clot lysis and degree of clot lysis.

FIG. 1 graphically depicts a sample testing cartridge 10 that includes a sample processing portion 12, a sample retention portion 14 and a suspension, e.g., beam 16 structurally, mechanically joining the sample retention portion 14 to the processing portion 12. The beam 16 shown in a cantilever configuration allows the sample retention portion 14 to act as a sprung mass relative to the sample processing portion 12 and to vibrate in response to a stimulus applied to the cartridge 10. Other structures, such as spring, multi-link suspensions, a rigid or semi-rigid member or members and the like capable of mechanically joining while allowing relative, dynamic movement of the sample retention portion to the sample processing portion may be used. It will be appreciated relatively small displacement, i.e., vibration of the sample is required. In certain embodiments, it may be possible to directly join the processing portion 12 and the retention structure 14 even forming them as an integral member.

The sample processing portion 12 includes a port 18 through which a liquid sample 100 may be introduced into the sample processing portion 12. The port 18 may be self-sealing (as in a septum or other automatic sealing mechanism) such that the sample once introduced into the cartridge 10 does not flow, leak, seep, etc. from the cartridge. The port 18 communicates with a reservoir 20 into which the sample is initially received. The sample processing portion 12 additionally includes channels, via, waste chambers, passages and similar structures 22; a bellows or pump 24 and valves 26 to control movement of the sample 100 or a portion thereof through the sample processing portion 12 responsive to actuation of the bellows 24 to prepare the sample 100 for testing.

Pneumatic force, which can be applied pressure, drawn vacuum or combinations thereof, and in a preferred implementation is vacuum, may be used directly on the sample 100 to move it into the cartridge 10 and to manipulate the various elements of the cartridge 10. In the illustrated implementation, vacuum applied at a central port 19 causes the sample 100 to load into a staging area 20 and further draws the sample 100 into the bellows 24. The sample 100 is drawn up to the hydrophobic vents 28, allowing careful control of the sample fluid volumes solely with the card geometry. As such, it is unnecessary to monitor loading time or otherwise actively sense of the volume of the sample 100, simplifying the structure and operation of the cartridge 10.

Application of vacuum to the bellows 24 and operation of selected valves 26 causes the sample portion 100 to be drawn from the staging area 20 and through and into a first passage 22'. The first passage 22' may include a testing reagent, in liquid, gel, lyophilized, dried or other suitable form that is reconstituted by, and then mixed with the sample portion 100 as it is drawn into and through the passage 22'. Cycling of the bellows 24 provides mixing of the sample and reagent by repeated communication of the sample 100 into and through the first passage 22'. Control of the valve 26 and actuation of the bellows 24 then allows communication of the conditioned sample portion 100 through a second passage 22" to the sample retention structure 14.

Bellows 24 operation to communicate the sample portion 100 through the cartridge 10 is not limited to operating the bellows in a binary fashion. Applying pneumatic pressure and/or vacuum to the bellow 24 via predetermined profiles, for example ramps, arcs and the like, provides a very controlled approach to the fluid flow profile within the sample processing portion 12 to limit fluid shear in the passages 22 which can lead to sample activation and furthermore to avoid bubble formation. Pneumatic inputs to the cartridge 10 and the bellows 24 through a flow restriction outside the card filters out pulsations caused by pulse-width-modulation (PWM) operation of the solenoid valve controlling the bellows 24.

Reagent reconstitution and mixing with the sample 100 may be accomplished by locating the reagent or multiple reagents at various locations within the cartridge 10 and exposing the sample portion 100 to the reagents. Reagents may be positioned at virtually any other location: wells, passages, via, chambers, bellows, and sample retainers, within the cartridge 10 where the reagents will contact the sample portion 100. Reagents may further be placed in the sample containment structure 30. For example, heparinase may be placed in the staging area 20 or other sample reservoir area of the cartridge 10. The sample portion 100 may then be drawn into the staging area 20 and allowed to remain in contact with heparinase for sufficient time to reconstitute the dried heparinase and counteract sodium heparin in the sample 100. This is prior to the sample 100 being pulled into the bellows and flowing through a reagent well, i.e., passage 22', where the treated sample 100 will contact other reagents. Spot reagents may be applied virtually anywhere on the cartridge, and additionally, reagent may coat the sample containing structure 30. Thus it will be appreciated that a cartridge 10 in accordance with various embodiments of the invention may have numerous different reagents located at numerous different locations of the cartridge in virtually any set of combinations.

U.S. Pat. No. 6,613,573 entitled Method and Apparatus for Monitoring Anti-Platelet Agents; U.S. Pat. No. 6,787,363 entitled Method and Apparatus for Hemostasis and Blood Management; U.S. Pat. No. 6,797,519 entitled Method and Apparatus for Diagnosing Hemostasis; U.S. Pat. No. 6,890,299 entitled Method and Apparatus for Monitoring Hemostasis in Connection with Artificial Surfaces Devices; U.S. Pat. No. 7,179,652 entitled Protocol for Monitoring Platelet Inhibition; U.S. Pat. No. 7,524,670 entitled Protocol for Risk Stratification of Ischemic Events and Optimized Individualized Treatment; U.S. Pat. No. 7,811,792 Protocol and Apparatus for Determining Heparin-induced Thrombocytopenia; U.S. Pat. No. 7,939,329 entitled Protocol for Risk Stratification of Ischemic Events and Optimized Individualized Treatment; U.S. Pat. No. 8,008,086 entitled Protocol for Monitoring Direct Thrombin Inhibition and U.S. Pat. No. 8,076,144 entitled Protocol for Risk Stratification of Ischemic Events and Optimized Individualized Treatment, the disclosures of which are hereby expressly incorporated herein by reference, teach a number of possible reagents and corresponding assays and protocols. The reagents may be as described in these patents or other reagents may be used, and/or the card may be configured to carry out other protocols.

The sample retention structure 14 communicates with the second passage 22 and includes a containing structure 30 for holding or containing the sample portion 100 during testing of the sample portion 100. For example, the sample retention structure 14 may include an annulus, cylinder, cup, or similar containing structure 30 that provides a sample surface free to be excited to resonant or near-resonant vibration and observed by a sensing device. One containing structure 30 includes a containing wall leaving two surfaces of the sample free to be excited to resonant or near-resonant vibration. The sample may be introduced to the containing structure 14 via a side port extending through the containing wall. The above-referenced U.S. Pat. Nos. 8,236,568; 7,879,615 and 7,261,861 describe several additional possible sample containing structures 30, all of which are contemplated suitable structures for use in an embodiment of the cartridge 10.

Figure 2:
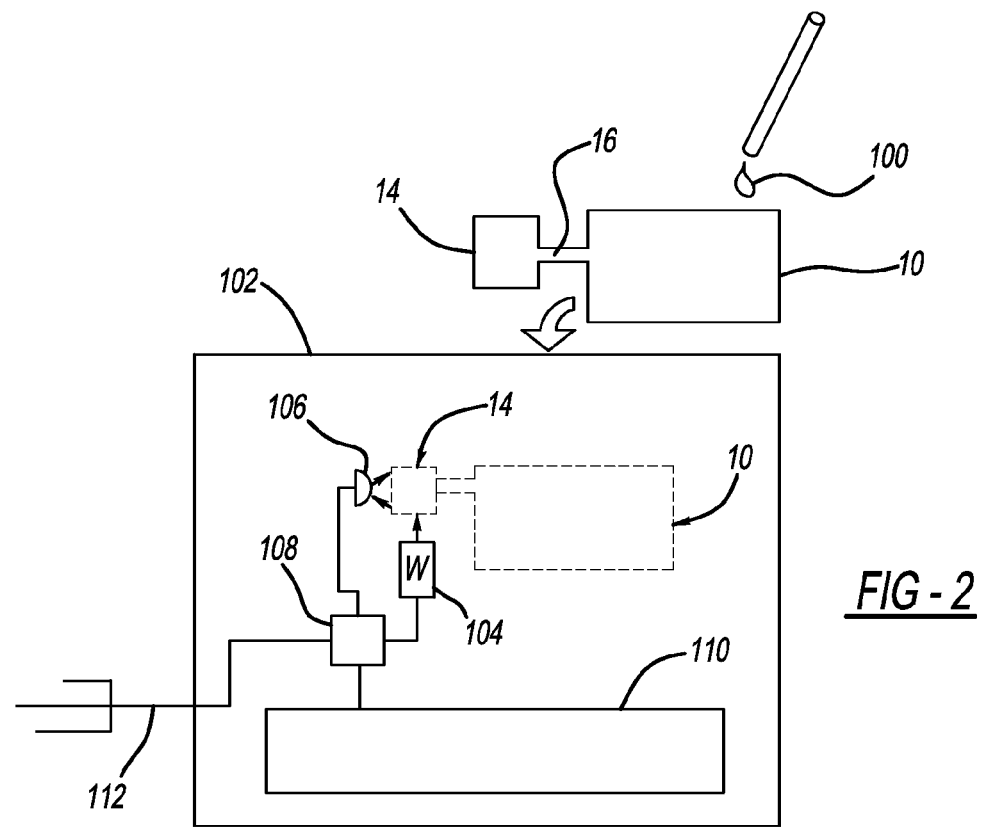
FIG. 2 is a schematic illustration of a hemostasis analyzer within which the cartridge of FIG. 1 may be used.

The cartridge 10 charged with a sample 100 is usable in an apparatus for measuring hemostasis 102. Depicted schematically in FIG. 2, the elements of the apparatus 102 are an exciter, shaker or similar stimulus generator 104, sensor/detector 106, processor 108, user interface 110 and communication link 112. A suitable power supply (not depicted) is provided. The exciter 104 can be a coil, piezoelectric device, motor, acoustic actuator or any suitable device to cause resonant excitation of the sample 100 within the sample retention apparatus 14 via direct stimulation of the retention apparatus 14 or indirectly via excitation of the cartridge 10 or a portion of the cartridge 10 or via combinations thereof. The sensor 106 may be an optical/laser device. The user interface 110 may be hard buttons, touch screen or any suitable interface to allow the user to select and initiate a testing protocol and to view or to affect recording or transmitting of the results. The processor 108 operably links these functional elements and facilitates communication by the communication link 112, which may be a wireless or wired network interface following any suitable protocol. For example, the communication link 112 may be used to communicate results data to a remote processing facility for analysis and diagnostic interpretation and to receive results analysis for display in data and graphic form via the user interface 110.

The cartridge 10 is placed within the testing apparatus 102. The blood sample 100, such as fresh whole blood, blood components, and the like is introduced into a reservoir 18 within the cartridge 10 via the port 20. The apparatus 102 is configured to selectively apply pneumatic signals, such as drawing a vacuum at a selected position of surface 32 of the cartridge 10 or actuating valves within the cartridge 10, in a predetermined testing protocol to condition the sample portion 100 by mixing with reagent and then communicating it to the sample retention structure 14.

The cartridge 10 may be built from laser-cut or die-cut layers laminated together to create functional elements: valves 26, bellows 24, channels 22 and fluid holding areas/reservoirs 18. It could also be assembled from injection-molded or hot-embossed layers that are then laminated, bonded or otherwise assembled together. Individual layers can be constructed in a number of ways, depending on when they enter the build sequence for the card.

The materials for each layer are chosen from suitable materials. For laser- and die-cut laminates, structural layers may be of a suitable plastic such as polyethylene terephthalate (PET), biaxially-oriented polypropylene (BOPP), cyclic olefin polymer (COP) or cyclic olefin copolymer (COC). Laminating adhesive may be provided separately or with structural layers. Flexible membrane layers, such as used to form valves, bellows and the like may be polyurethane, silicone, polypropylene (PP) or polyethylene (PE). Conventional conversion techniques may be used to prepare the layers when they are composed of more than one material.

Hydrophobic membrane material and sizes, along with layout of the cartridge, may be chosen to reduce the cost of material used per card, and allow for easier automatic placement of the membranes in the finished cartridge 10.

The size of the pores and thickness of the material may be used to control the blood flow rate and volume into the card and into the bellows. Channels leading to the membranes may be low volume to reduce sample or reagent loss. In the instant application, this is done to reduce blood sample loss and prevent errors in reagent concentration. Other channels may be of higher volume to facilitate sample communication within the card, and for example to the sample retention structure 14.

In one embodiment, the channel size communicating to the sample retention structure 14 may be made to be 0.017 square millimeters or greater in cross-section, to facilitate flow of the processed sample to the sample retention structure without significant shear activation of platelets within the sample or unintended activation as a result of both shear and exposure to reagent. Suitable dimensions of 0.20 square millimeters or greater, and for example, 0.30 square millimeters may be used.

Figure 3:
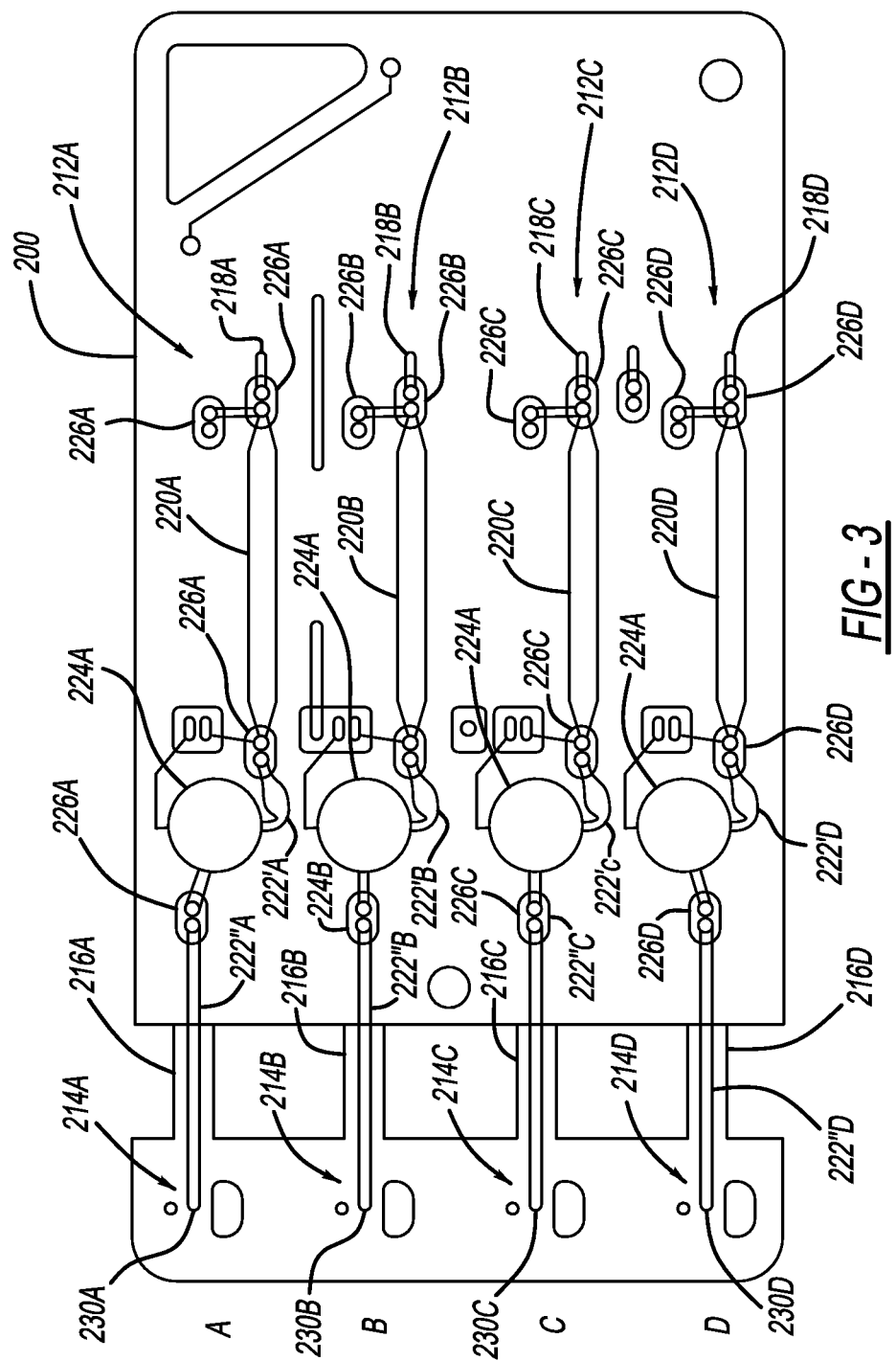
FIG. 3 graphically depicts a cartridge for sample testing in accordance with a herein described alternate embodiment of the invention.

FIG. 3 graphically illustrates a cartridge 200 that may be used in sample testing, such as in hemostasis sample testing of a whole blood or blood component sample. The cartridge 200 has features similar to that of cartridge 10, but provides potential for multiple simultaneous tests. That is, each channel on the cartridge may contain different reagents and hence constitute different tests or may be configured to provide redundant tests. The combined tests may constitute an assay. The cartridge 200 is configured to perform up to four (4) tests simultaneously. Although, in use any combination from one (1) to four (4) tests may be performed. Cartridge 200 also demonstrates that a cartridge may be made with virtually any number of tests, with FIG. 1 and FIG. 3 demonstrating at least single test cartridges and four (4) test cartridges, cartridges of 2 or 3 tests may be made as well as cartridge having more than four (4) tests may be made. A channel or channels of the cartridge may be a test or tests to test a specific characteristic of hemostasis that may be used in an assay of such hemostasis related characteristics, such as platelet activity, ischemic risk indicators, or the like as set forth in the afore-mentioned US patents. The cartridges 200 may be configured to provide multiple tests or may be made to provide the same tests with multiple different samples, or combinations thereof.

As seen in FIG. 3, the cartridge 200 is formed with four (4) tests A, B, C and D. Each test on the cartridge 200 includes a sample processing portion 212, a sample retention portion 214 and a suspension, e.g., beam 216 structurally, mechanically joining the sample retention portion 214 to the processing portion 212. The elements of the respective tests are indicated separately by the alpha designation A, B, C or D. The plurality of beams 216 shown in cantilever configuration allow the sample retention portion 214 to act as a sprung mass relative to the sample processing portion 212 and to vibrate in response to a stimulus applied to the retention structure 214 and/or the cartridge 200. Other structures, such as spring, multi-link suspensions, a semi-rigid mechanical member or members and the like capable of mechanically joining while allowing relative, dynamic movement of the sample retention portion to the sample processing portion may be used. It will be appreciated relatively small displacement, i.e., vibration of the sample is required. In certain embodiments, it may be possible to directly join the processing portion 212 and the retention structure 214 even forming them as an integral member.

The sample-processing portion 212 may include a common port feeding through a plenum or manifold or individual ports 218 through which a liquid sample 100 may be introduced into the tests of the sample processing portion 212. The ports 218 may be self-sealing such that the sample once introduced into the cartridge 200 does not flow, leak, seep, etc. from the cartridge. The ports 218 communicate with respective reservoirs or sample holding areas 220 into which the sample is initially received. The sample-processing portion 12 additionally includes, channels, via, passages and similar structures 222; bellows or pumps 224 and valves 226 to control movement of the sample 100 or a portion thereof through the sample processing portion 212 responsive to actuation of the bellows 224 to prepare the sample 100 for testing. Application of external pneumatic pressure to the bellows 224 and operation of selected valves 226 causes the sample portion 100 to be drawn from the reservoir 220 and through and into a first passage 222' and the bellows 224. The first passage 222' may include a testing reagent, in liquid, gel, lyophilized or dried form that is mixed with the sample as it is drawn into and through the passage 222'. As described herein, reagents may be located at other locations of the cartridge 200. Cycling of the bellows 224, which may be accomplished as described by above via pulse-width modulation of the pressure and vacuum signals, allows mixing of the sample and reagent by repeated communication of the sample 100 into and through the first passage 222'. Control of the valve 226 and actuation of the bellows 224 then allows communication of the conditioned sample portion 100 through a second passage 22" to the sample retention structure 214 and sample containment structure 230. Suitable waste chambers are provided within the cartridge to ensure containment of the sample.

The cartridge 200 charged with samples 100 is then prepared and ready to be introduced into a testing apparatus to perform the tests or tests for which the cartridge is configured and to report the respective results.

Figure 4:
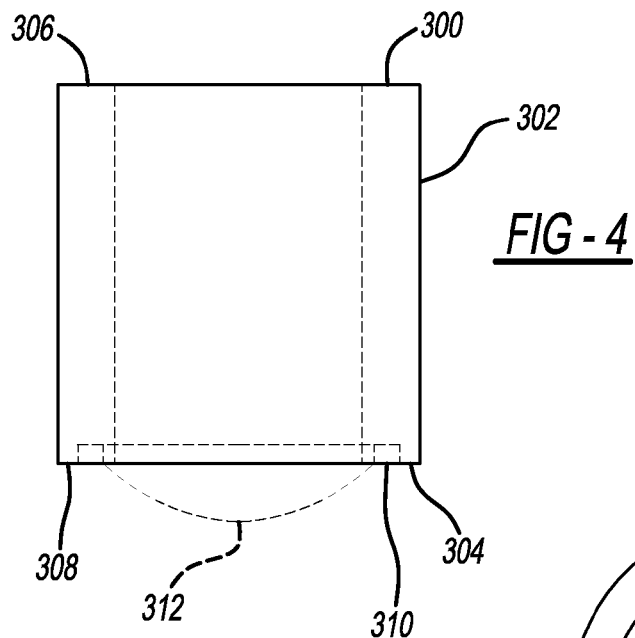
FIG. 4 is a front view of a sample containment structure according to a herein described embodiment.
Figure 5:
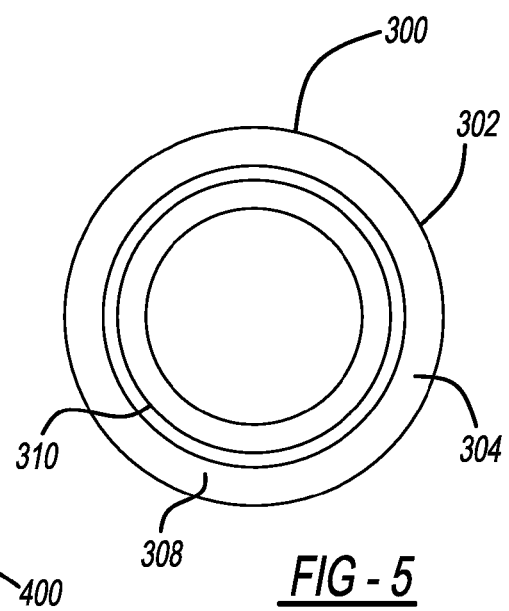
FIG. 5 is an end view of the sample containment structure shown in FIG. 4.

FIGS. 4 and 5 illustrates a sample retention structure 300 that may be used in any of the cartridges 10 or 200 as the respective sample retention structures 30 and 230. The sample retention structure 300 has an annulus body 302 with a first end 304 and a second end 306. The first end 304 had an end surface 308 within which is formed a relief 310 about the entire circumference. A liquid sample, such as whole blood or blood components is introduced into the sample retention structure 300, for example through a side port not depicted, and is driven into the body 302 by controlled compression or activation of the bellows 224 toward the first end 304. The annulus 302 is overfilled to ensure all interior surfaces are wetted by the sample, and then the sample volume in the annulus is reduced to form a convex surface 312 (shown in phantom) extending from the first end 302. It is this convex surface 312 that is observed as the sample within the annulus 302 is set into resonant oscillation as a result of stimulation of the cartridge 10/200. The diameter of the relief 310 also helps to establish a consistent volume of sample, along with other geometry of the cartridge and control of the fluid processing structures, to be placed into resonant oscillation, and thus complex calibration processes are not required.

While it is possible to observe the entire convex surface 312, observing only a portion of the free surface may be sufficient to yield a usable result. For example, a center portion of the convex surface 312 may be observed.

Figure 6:
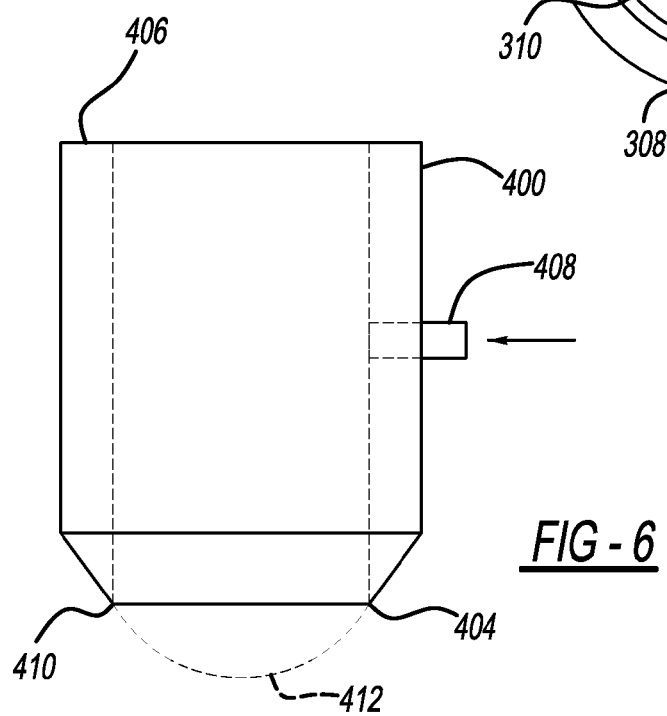
FIG. 6 is a front view of a sample containment structure according to a herein described embodiment.

FIG. 6 illustrates a sample retention structure 400 that may be used in any of the cartridges 10 or 200 as the respective sample retention structures 30 and 230. The sample retention structure 400 has an annulus body 402 with a first end 404 and a second end 406. The first end 404 has an end surface 408 formed to an edge structure 410 about the entire circumference. The edge structure 410 may be substantially planar, that is, all points about the edge structure 410 being substantially within a common plane. A liquid sample, such as whole blood or blood components, is introduced at a side port 412 and is driven into the body 402 by controlled compression or activation of the bellows 224 toward the first end 404. The annulus 402 is overfilled to ensure all interior surfaces are wetted by the sample, and then the sample volume in the annulus is reduced to form a convex surface 412 (shown in phantom) extending from the first end 402. It is this convex surface 312 that is observed as the sample within the annulus 402 is set into resonant oscillation as a result of stimulation of the cartridge 10/200.

While the structures 300 and 400 are shown as circular cylinders, the sample retention structure is not limited in its shape. The sample retention structure need only have a wall structure, e.g., wall 314 or wall 414 of the respective structures 300 and 300, to contain the sample but leaving the sample with at least two free surfaces permitting observable resonant vibration of the sample. For example, the sample retention structure may be oval, prismatic, conical, or virtually any other suitable structure and geometric shape that permits excitation of the sample to resonant vibration and observation of the motion of the sample in response to the excitation.

Figure 7:
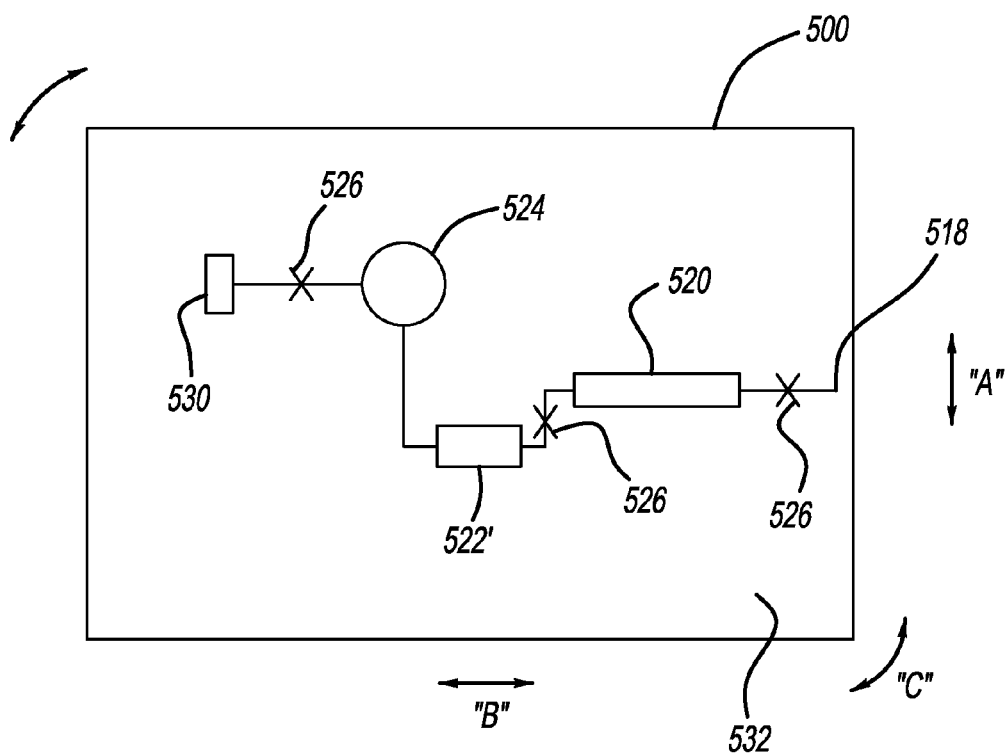
FIG. 7 graphically depicts a cartridge for sample testing in accordance with a herein described embodiment of the invention.

FIG. 7 illustrates a cartridge 500, which is similar to cartridge 10 in that it is configured for a single test although it could be configured for multiple tests, such as is the case with cartridge 200. The sample testing cartridge 500 includes a sample processing portion 512, a sample retention portion 514 within a card body 516.

The sample-processing portion 512 includes a port 518 through which a liquid sample, such as the previously described sample 100, may be introduced into the sample-processing portion 512. The port 518 may be self-sealing (as in a septum or other automatic sealing mechanism) such that the sample once introduced into the cartridge 500 does not flow, leak, seep, etc. from the cartridge. The port 518 communicates with a reservoir 520 into which the sample is initially received. The sample processing portion 512 additionally includes channels, via, waste chambers, passages and similar structures 522; a bellows or pump 524 and valves 526 to control movement of the sample 100 or a portion thereof through the sample processing portion 512 responsive to actuation of the bellows 524 to prepare the sample 100 for testing.

Pneumatic force, which can be applied pressure, drawn vacuum or combinations thereof, and in a preferred implementation is vacuum, may be used directly on the sample 100 to move it into the cartridge 500 and to manipulate the various elements of the cartridge 500. In the illustrated implementation, vacuum applied at a central port 519 causes the sample 100 to load into a staging area 520 and further draws the sample 100 into the bellows 524. The sample 100 is drawn up to the hydrophobic vents 528, allowing careful control of the sample fluid volumes solely with the card geometry. As with the cartridges 10 or 200, it is unnecessary to monitor loading time or otherwise actively sense of the volume of the sample 100, simplifying the structure and operation of the cartridge 500. Likewise, the sample is prepared for in a manner as described above and communicated to a sample retention structure 514.

To excite the sample 100 within the cartridge 500, an exciting stimulus may be applied to the entire cartridge 500. Arrows "A", "B" or "C", indicate single or multiple excitation of the cartridge, and hence the sample, rotational excitation of the cartridge or combinations thereof. Excitation of the cartridge 500 results in corresponding excitation of the sample 100 to resonance, which in turn is observed in order to derive hemostasis characteristics.

Although certain apparatus constructed in accordance with the teachings of the invention and methods have been described herein, the scope of coverage of this patent is not limited thereto. Generally, apparatus and methods are provided yielding for the first time continuous, accurate results starting from liquid blood and following the transition to a gel state. Observation of the increasing resonant frequency of the sample provides a direct measure of the elastic properties of the material and corresponding hemostasis characteristics.

This patent covers all examples of the teachings of the invention fairly falling within the scope of the appended claims either literally or under the doctrine of equivalents.

We claim:

1. A method of testing blood hemostasis comprising:
   introducing a blood sample into a fluid processing structure, the fluid processing structure having a portion containing a reagent;
   processing at least a portion of the blood sample within the fluid processing structure by contacting the portion with the reagent;
   communicating the processed portion to a sample retention structure portion of the fluid processing structure; and
   testing the processed portion by: exciting to resonant excitation the processed portion within the sample retention structure portion and measuring the the processed portion at resonant excitation to obtain data, the data being indicative of at least one hemostasis parameter.

2. The method of claim 1, wherein reagent is disposed within a passage of the fluid processing structure, and processing comprises passing the portion through the passage.

3. The method of claim 2, wherein the fluid processing structure comprises a pump and wherein passing the portion through the passage comprises pumping the portion through the passage.

4. The method of claim 3, wherein pumping the portion through the passage comprises a predetermined flow profile.

5. The method of claim 4, wherein the predetermined flow profile comprises at least one of a step, a ramp and an arc.

6. The method of claim 4, wherein the predetermined flow profile is selected to reduce shearing of the blood sample.

7. The method of claim 1, wherein one or more reagents is disposed in one or more fluid communicating portions or passages of the fluid processing structure, and processing comprises communicating the portion through the communicating portions or passages.

8. The method of claim 1, wherein one or more reagents is disposed in one or more fluid communicating portions or passages of the fluid processing structure, and processing comprises contacting the blood sample with a reagent in at least one reagent containing portion of the fluid processing structure.

9. The method of claim 1, wherein communicating the processed portion to the sample retention structure portion comprises pumping the sample to the sample retention structure portion.

10. The method of claim 1, the fluid processing structure comprising first and second passages, and processing comprises passing a first portion of the blood sample through the first passage and passing a second portion of the blood sample through the second passage.

11. The method of claim 10, comprising communicating the processed first portion to a first sample retention structure portion and communicating the processed second portion to a second sample retention structure portion, and simultaneously testing the processed first portion to obtain a first hemostasis parameter, and testing the processed second portion to obtain a second hemostasis parameter.

12. The method of claim 1, wherein testing comprises exciting the processed portion to resonant vibration.

13. The method of claim 12, wherein the hemostasis parameter comprises at least one of: time to initial clot formation, rate of clot formation, maximum clot strength and degree of clot lysis.

14. The method of claim 1, comprising communicating the data via a network.

15. The method of claim 1, comprising graphically depicting the data.

16. The method of claim 1, the fluid processing structure and the sample retention structure being portions of a cartridge, and wherein testing the processed portion by resonant excitation comprises applying an excitation to the cartridge.

17. The method of claim 1, the fluid processing structure and the sample retention structure being portions of a cartridge, and wherein testing the processed portion by resonant excitation comprises applying an excitation to a portion of the cartridge containing the sample retention structure.

18. The method of claim 1, the method comprising sizing the portion of the blood sample by selectively filling a portion of the fluid processing structure having a certain, predefined volume.

19. The method of claim 1, the method comprising sizing the portion of the blood sample by providing within the fluid processing structure a certain, predefined volume.

20. The method of claim 1, the method comprising observing a portion of the processed portion during resonant excitation using a non-contact, optical sensor.

21. The method of claim 1, wherein exciting to resonant excitation the processed portion within the sample retention structure portion, comprises exciting to resonant excitation a free surface of the processed portion within the sample retention structure portion.

* * * * *